(12) United States Patent
Peter et al.

(10) Patent No.: US 6,407,306 B1
(45) Date of Patent: Jun. 18, 2002

(54) PROCESS FOR EXTRACTING CAROTENES FROM CAROTENE-CONTAINING MATERIALS

(75) Inventors: Siegfried Peter, Lindenweg 3, Uttenreuth-Weiher (DE), D-91080; Martin Drescher, Nuremberg; Eckhard Weidner, Bochum, both of (DE)

(73) Assignee: Siegfried Peter, Uttenreuth-Weiher (DE)

( * ) Notice: Subject to any disclaimer, the term of this patent is extended or adjusted under 35 U.S.C. 154(b) by 21 days.

(21) Appl. No.: 09/709,823

(22) Filed: Nov. 10, 2000

(51) Int. Cl.[7] .......................... C07C 403/00; C07C 7/10; C07C 7/00
(52) U.S. Cl. ..................... 585/833; 585/862; 585/860; 585/864; 585/351
(58) Field of Search ................................ 585/833, 860, 585/862, 864, 351

(56) References Cited

FOREIGN PATENT DOCUMENTS

| EP | 242148 | 10/1987 | |
|----|--------|---------|--------|
| EP | 670306 | 9/1995 | ................ 403/24 |
| WO | 9629306 | 9/1996 | ................ 403/24 |
| WO | 9803480 | 1/1998 | ................ 403/24 |

*Primary Examiner*—Walter D. Griffin
*Assistant Examiner*—Tam M. Nguyen
(74) *Attorney, Agent, or Firm*—Klauber & Jackson

(57) ABSTRACT

A process is described for extracting carotenes from carotene-containing materials, in particular from fats and oils of biological origin, which provides for extraction of carotene-containing material with an extractant comprising at least one member selected from the group consisting of acetonitrile, N-methylpyrrolidone, N,N-dimethylformamide, N,N-dimethylacetamide, 4-formylmorpholine, 4-acetylmorpholine, 4-methylmorpholine, 4-phenylmorpholine.

21 Claims, No Drawings

PROCESS FOR EXTRACTING CAROTENES FROM CAROTENE-CONTAINING MATERIALS

CROSS-REFERENCE TO RELATED APPLICATIONS

This application claims benefit of priority under 35 U.S.C. §120 to International Application PCT/EP99/03219, filed May 11, 1999, and under 35 U.S.C. §119 to DE19821009.4, filed May 11, 1993.

The present invention relates to a process for extracting carotenes from carotene-containing materials, in particular from fats and oils of biological origin. though the invention shall chiefly be explained through the example of carotene, the term "carotenes" encompasses not only the isomers of carotene but also carotenoids.

According to a definition by IUPAC, carotenoids are chemical compounds of aliphatic or aliphatic-alicyclic structure having conjugated double bonds and comprising 3 to 8 (or even more) isoprene moieties.

The carotenoids are the most important group of natural colouring materials most widely occurring in plants and animals. They are fat-soluble, nitrogen-free, yellow to violet materials, wherein the uninterrupted sequence of isoprene moieties and thus the chromophoric accumulation of conjugated double bonds gives rise to colouring. All carotenoids being polyenes, they exhibit a blue solution color in concentrated sulphuric acid.

Carotene is the carotenoid which has been known for the longest time. It was isolated for the first time by H. Wackenroder (in 1831) from carrots. About 100 years after its discovery, Kuhn found in 1931 that the naturally occurring carotene is composed of three isomers which he named α carotene, β-carotene and γ-carotene. In the untreated carotene of carrots, they are contained at proportions of about 15, 85, and 0.1%, respectively. Ever since the first carotenoid syntheses by P. Karrer and H. H. Inhoffen (1950), a rapid development commenced in the field of commercial syntheses of carotenoids.

All three carotene isomers possess the same fundamental structure, comprising one β-ionone ring structure at one molecule end, 9 conjugated double bonds and 8 branchings. They differ only in the structure of the other molecule end.

Depending on its origin, carotene is a varying mixture of the structurally isomeric polyene hydrocarbons $C_{40}H_{56}$: all-trans-α-carotene, all-trans-β-carotene, all-trans-γ-carotene. Depending on processing and starting material, cis isomers may also occur.

Carotene occurs not only in carrots but also in numerous other plants, and particularly accompanying chlorophyll it counts among the most frequently occurring plant coloring materials. Carotenes are present in vegetable oils at moreor less elevated concentrations. The carotene contents are particularly high in palm oil, in the ranging from 0.05 to 0.2%.

Raw carotene is a dark coppery to cinnabar-colored crystal powder of wax-like consistency. Its solution color is yellow to orange.

β-Carotene is the carotene occurring most frequently in animals and vegetables. It forms deeply violet prisms (crystallised from benzene/methanol) or polyhedra (from petroleum ether). Its solubility in grams per 100 $cm^3$ of solvent at 19° C. is 5.5 in carbon disulfide; 0.35 in benzene; 0.1 in petroleum ether; 0.008 in ethanol. It is optically inactive. α-Carotene forms deeply violet prisms (from benzene/methanol) or polyhedra (from petroleum ether). It is optically active and more readily soluble than β-carotene. γ-Carotene forms dark red prisms (from benzene/methanol). It is optically inactive and also more readily soluble than β-carotene.

Carotene is merchandised in the form of the following preparations: crystallised β-carotene in vacuum ampoules; technically crystallised at about 80%; carotene concentrates in powder form at about 3%; carotene solutions in vegetable oils at about 0.3 to 0.5%.

Carotenes, being polyene hydrocarbons, exhibit good solubility in tetrahydrofuran, carbon disulfide, benzene, chloroform and oils, low solubility in ether and petroleum ether. All carotenes are insoluble in water. In fats and oils of biological origin, their solubility typically is 2 to 3%. Almost all carotenes have high melting points (e.g., β-carotene 183° C.). They are sensitive to acids, oxygen and exposure to light.

The carotenes, have gained importance in nutrient technology as antioxidants and as natural colouring materials. They predominantly serve for coloring fats and oils, for vitamin enrichment of margarine, nutrient preparations, and pharmaceuticals, as an addition to concentrated feed in rearing young animals and to ice creams or sherbets and milk preparations.

The carotenoids, being hydrocarbons or compounds closely related to hydrocarbons, are markedly lipophilic. (Carotenoids of the polyene alcohol type dissolve well in alcohol and acetone.) All-trans forms do not dissolve as well as corresponding cis compounds. Carotenoids occur in nature almost exclusively in solution in the lipoid particles of the cell, for which reason they are at times referred to as lipochrome colouring materials. From the dried cell substance they can be extracted only by means of lipophilic solvents. The commonly known fact that the carotenoids of our nutrient plants, e.g., the lycopene of the tomato, enrich in the fat globules of the foods prepared from them, is founded in this lipophilic character.

H. V. Euler realised (in 1928) the property of carotene being provitamin A. β-Carotene is related to vitamin A, which latter one may be conceived to be formed by cleavage of the central C=C double bond of the carotene with concomitant incorporation of two molecules of water. Biosynthesis of vitamin A also appears to unfold in this way. At least the animal body is capable of transforming in most cases carotene, especially β-carotene, into vitamin A. This is of interest inasmuch as a vitamin A deficiency may be remedied through easily obtained foods which contain carotene.

For obtaining the carotene, the natural material is dried mostly at temperatures below 50° C., and the carotenes are extracted with lipophilic solvents. Jointly dissolved accompanying substances are separated out either by saponification or by freezing out. Crystallised raw carotene (75–90%) or oil-based carotene concentrates (1–20%) are obtained. Of the isomers, only β-carotene is obtained pure. Starting products are either such having a high carotene content, like carrots (1 g of raw carotene/kg of dry substance), raw palm oil (up to 3 g/kg), pumpkin seeds or green plants such as lucerne (alfalfa), stinging nettle or broccoli (Brassica), from which xanthophyll and chlorophyll are furthermore obtained besides carotenes.

For the extraction of carotenes from dry plants, petroleum ether, naphtha, less frequently benzene, fatty oils are used, or also trichloroethylene in the case of red palm oil. For obtaining them from carrots, autumn carrots [Herbstmöhren] are suited best, which should contain at least 10 mg %

[mg/100 ml] of carotene for 10–15% dry substance. One starts out from dried carrots (dry processing method) or from material processed in the autoclave and pressed hydraulically (wet processing method). The dry method procures a yield of 67 g of carotene/1000 kg of carrots. In the wet method, extraction is performed with tetrahydrofuran and provides a yield of 62–72 g of carotene from 1000 kg of carrots having a carotene content of 90–100 g.

The most important cultivation areas for oil palms are Africa, Indonesia, Malaysia and Brazil. Depending on their origin and freshness condition, palm oils have a bright yellow (predominantly α-carotene), red (lycopene), orange (predominantly β-carotene) or reddish brown (presence of chlorophyll) coloration. In general, the raw oil is processed with alkali into low-water soaps from which the carotenoids are extracted with benzene, trichloroethylene or petroleum ether. The yield is approximately 80–90% of the overall carotenoids of the oil. From 1000 kg of palm oil, one obtains about 3–4 kg of carotene extract (containing 20% carotene, 6.5% lycopene and 6% volatile oils).

The recovery of the carotenes present in oils and fats by way of saponification of the glycerides and subsequent extraction of the carotenes from the soaps with lipophilic solvents is a costly process. Moreover carotenes from fats and oils, which pass into the food sector without being chemically modified, are not accessible in this way.

DE-A-195 31 245 discloses a process for the extraction of carotenes, in particular β-carotene, from solid biological materials by means of a liquid organic extractant mixture consisting of ethyl acetate and/or butyl acetate and 3 to wt. % of an oil of biological origin, relative to the ethyl acetate and/or butyl acetate, at temperatures between 40 and 125° C.

DE-A-44 29 506 discloses a process for the extraction of carotenoids from natural starting materials by means of dense gases, wherein the pre-dried natural starting material is extracted with dense propane and/or dense butane, optionally in the presence of an organic entrainer, at temperature between 20 and 100° C. and pressures between 10 to 200 bar.

EP-A-0 455 425 discloses a process for the preparation of concentrates of coloring agents, wherein said concentrates of natural coloring agents such as carotene are prepared from organic media, particularly from palm oil, by a process in which the oil, together with a volatile solvent, is subjected to gel permeation chromatography.

EP-A-0 242 148 discloses a method for purification of a carotene-containing concentrate by chromatography in which a liquid containing a carotene-containing concentrate is fed to a filler to adsorb the concentrate on the filler, and the carotene component is subsequently eluted and collected by feeding an eluant to the filler.

EP-A-0 239 949 discloses a process for the manufacture of powdery, finely divided preparations of carotenoids in which the carotenoid essentially has a particle size of less than 0.5 μm, comprising dissolving the carotenoid in a volatile, water-miscible organic solvent at temperatures between 50 and 240° C., under atmospheric or superatmospheric pressure, in less than 10 seconds, and precipitating the dissolved carotenoid in colloidal disperse form by rapid mixing with milk at from 0 to 50° C.

WO-A-98/03480 discloses a process for recovering highly pure β-carotene crystals from a crude crystal preparation obtained from a natural source. To remove impurities, the crude crystals are stirred in a solvent in which β-carotene has a low solubility, whereupon the crystals are filtered off and washed with fresh solvent. Using this process, a natural crystalline β-carotene preparation with a very high purity is obtained.

WO-A-96/29306 discloses a process for the recovery of carotene from native fat or oil, in particular from palm oil, wherein the native fat or oil is converted with an alkanol with a C chain length of up to 4 catalytically into fatty alkyl ester and glycerine in a prior art manner. The ester phase of the reaction mixture is subjected to distillation to separate the fatty acid alkyl ester. The distillation residue obtained in the second step is saponified, carotene is extracted from the product obtained in the third step and the extract phase is concentrated by evaporation. A yield of at least some 80% is obtained. At the same time a fatty acid alkyl ester is provided for further processing into fatty alcohol.

JP-A-09048927, Patent Abstract of Japan, discloses a process to provide a high-quality odorless carotenoid pigment used for foods, drugs, quasi-drugs and cosmetics by removing the inherent characteristic odor and contaminants from a material containing a carotenoid pigment, wherein a purified carotenoid pigment is obtained by mixing a material containing 1% or above carotenoid with a water-soluble organic solvent and then with a fat-soluble organic solvent or by mixing the material with a fat-soluble organic solvent and then with a water-soluble organic solvent.

A method was sought to obtain the carotenes by direct extraction of carotene-containing materials, in particular of fats and oils of biological origin.

Subject matter of the present invention is a process for extracting carotenes from carotene-containing materials, which comprises extracting a carotene-containing material with an extractant comprising at least one member selected from the group consisting of acetonitrile, N-methylpyrrolidone (NMP), N,N-dimethylformamide (DMF), tetrahydrofuran, N,N-dimethylacetamide, furfurol, morpholine, 4-formylmorpholine, 4-acetylmorpholine, 4-methylmorpholine (NMM), 4-phenylmorpholine, with the formation of two liquid phases, one of which is a carotene-depleted raffinate phase and the other one is a carotene-enriched extract phase; and separating the two liquid phases.

There is a large number of carotene-containing materials, in particular fats and oils of biological origin, to which the method according to the invention is applicable and which have economically interesting contents of carotenoids. Palm oil is particularly preferred in this context. Further examples to be named include: soybean oil, rapeseed oil, corn oil, hemp oil, sunflower oil, olive oil, linseed oil, beet oil, castor oil, sesame oil, cocoa butter, rice germ oil, cottonseed oil, grape kernel oil, wheat germ oil, palm kernel oil, coconut oil, peanut oil, safflower oil, and mixtures thereof.

The extraction according to the present invention is preferably performed in countercurrent flow. This allows to exploit even small differences in distribution coefficient.

The extractant dissolved in the raffinate phase and/or the extract phase may (preferably between room temperature and 50° C., however above the melting point of the fat or oil) be removed by liquid-liquid extraction with water. As a result of the very high distribution coefficient, high concentrations of the extractant in the aqueous solution may hereby be obtained. By rectification, the water and the extractant may be separated from each other. The recovered extractant may be recirculated.

Another possibility of purifying the raffinate phase and/or extract phase with respect to the extractants consists in removing the extractant from raffinate phase and/or extract phase by stripping with nitrogen, steam (steam distillation) or alcohol vapor, selected from among methanol vapor, ethanol vapor and isopropanol vapor, preferably under reduced pressure.

Moreover the extractant may be removed from the raffinate phase and/or extract phase by extraction with dense gases, selected from the group consisting of carbon dioxide, propane, propene, butane and mixtures thereof, preferably under near-critical conditions. As an example, 4-formylmorpholine is soluble at 70° C. and 120 bar at a concentration of 9 wt. % in carbon dioxide.

Near-critical conditions, in the framework of this invention, preferably comprise reduced temperatures of from about 0.7 to about 1.3. The term "reduced temperature" is defined by the equation: $T_r=T/T_c$, wherein $T_r$ is the reduced temperature, T is the actual working temperature and $T_c$ is the critical temperature of the respective gas. The unit of T and $T_c$ is Kelvin [K]. $T_r$ does not have a unit, therefore. Butane, for instance, exhibits a reduced temperature of about 0,69 at room temperature.

The carotenes enriched in the extract phase may be recovered from said extract phase by crystallization and filtration. Preferably the filtered-off carotenes are commercialised while still oil-wet because pure carotenes have a tendency to undergo violent polymerisation reactions. The carotenes obtained in this way may, however, also be purified in accordance with conventional methods and sealed in vacuum ampoules. The remaining, carotene-saturated oil may be commercialised as such. As an alternative, this oil might also be recycled.

Various extractants, such as, for example, dimethylformamide, 4-formylmorpholine, etc., form two-phase systems with most oils and fats without the addition of auxiliary agents.

Where required, small quantities of water or of an alkanol entirely miscible with water, preferably methanol, are added to the extractants in order to bring about a two-phase condition.

Another option of establishing a two-phase condition in the systems of the extractants and the carotene-containing oil or fat consists in adding carbon dioxide, propane, propene or butane under elevated pressure to the mixture. Herein pressure and temperature are selected such that the binary system of gaseous components and solvent is single-phase, i.e., supercritical.

A third method for reducing the mutual solubility of extractant and oil is to add an alkane such as, for example, propane, butane, heptane or petroleum ether to the oil. Dimethylformamide and 4-formylmorpholine, for example, are miscible with most organic solvents with the exception of aliphatic hydrocarbons and glycerol triesters.

The slimy substances, solids, and free fatty acids are preferably removed in a maximum possible degree by degumming, filtration and deacidification, as well as combinations of these pretreatments. Oxygen should suitably also be removed beforehand.

The fat or oil of biological origin, prior to the extraction, may optionally be subjected to a preliminary extraction with a solvent selected from among methanol, ethanol, ethanol/water, isopropanol, isopropanol/water and mixtures thereof. However, this is not a prerequisite for the extraction according to the present invention.

As extractants for the extraction according to the invention, mixtures of N-methylpyrrolidone and methanol, preferably containing 30–70 wt. % methanol, in particular 40–60 wt. % methanol, or mixtures of 4-methylmorpholine and water, preferably containing 3–20 wt. % water, in particular 5–15 wt. % water, have been found to be well suited.

Extractants which are particularly well suited for the extraction according to the present invention are 4-formylmorpholine and mixtures of 4-formylmorpholine and methanol, preferably containing 5–30 wt. % methanol, in particular 5–10 wt. % methanol.

Extraction in accordance with the invention is preferably performed at temperatures in the range of from about 20 to about 120° C., preferably in the range of from about 40 to about 80° C. One suitably operates above the melting point of the respective fat or oil.

The following description of the method is given by way of examples without, however, thereby restricting the claims. Percentages and ppm indications relate to weight.

EXAMPLE 1

100 g of palm oil containing 320 ppm carotene and 4.4 wt. % free fatty acids was mixed thoroughly with 50 g of N-methylpyrrolidone and 50 g of methanol in a vessel at 60° C. by stirring. Following interruption of the mixing process and separation of the two liquid phases, samples were taken from either phase and analysed. The raffinate phase (i.e., the oil-rich phase) minus the extractant contained 2.9 wt. % free fatty acids and 300 ppm carotene. The extract phase minus the extractant contained 8.6 wt. % free fatty acids and 370 ppm carotene.

EXAMPLE 2

100 g of palm oil containing 380 ppm carotene and 4.1 wt. % free fatty acids was mixed thoroughly with 87.5 g of 4-methylmorpholine and 12.5 g of water in a vessel at 60° C. by stirring for 15 minutes. Following interruption of the mixing process, separation of the two liquid phases was allowed to take place, and then samples were taken from either phase and analysed. The raffinate phase minus the extractant contained 3.6 wt. % free fatty acids and 360 ppm carotene. The extract phase minus the extractant contained approx. 65 wt. % free fatty acids, approx. 35 wt. % glyceride and 1030 ppm carotene. The quantity of extract phase amounted to 2.8 g, corresponding to a loading of the extractant of approx. 3 wt. %.

EXAMPLE 3

100 g of deacidified palm oil with a residual free fatty acids content of 0.28 wt. % and a carotene content of 420 ppm was mixed thoroughly with 12.5 g of water and 87.5 g of 4-methylmorpholine in a vessel at 60° C. by stirring. Following interruption of the mixing process, separation of the two liquid phases was allowed to take place, and then samples were taken from both phases and analysed. The raffinate phase minus the extractant contained 0.11 wt. % free fatty acids and 361 ppm carotene. The extract phase minus the extractant contained approx. 71.3 wt. % neutral oil (glycerides), approx. 27.6 wt. % free fatty acids and 1150 ppm carotene.

EXAMPLE 4

100 g of deacidified palm oil with a residual free fatty acids content of 0.47 wt. % and a carotene content of 290 ppm was mixed thoroughly with 6 g of water and 94 g of 4-methylmorpholine in a vessel at 60° C. by stirring. Following interruption of the mixing process, separation of the two liquid phases was allowed to take place, and then samples were taken from both phases and analysed. The raffinate phase minus the extractant contained 0.36 wt. % free fatty acids and 280 ppm carotene. The extract phase minus the extractant contained approx. 96.8 wt. % neutral oil, 3.2 wt. % free fatty acids and 480 ppm carotene.

EXAMPLE 5

200 g of deacidified palm oil with a carotene content of 420 ppm, a tocopherol content of 290 ppm, a tocotrienol content of 590 ppm and a free fatty acids content of 0.1 wt. % was mixed with 200 g of methanol by stirring. Following interruption of the mixing process, separation into two liquid, co-existing phases was allowed to take place, and samples were taken from either phase for analysis. The oil-rich raffinate phase minus the methanol contained 416 ppm carotene, 0.03 wt. % free fatty acids, 10 ppm tocopherol, 25 ppm tocotrienol and 10 ppm sterols dissolved in neutral oil. The extract phase minus the methanol contained 1 wt. % free fatty acids, 173 ppm carotene, 530 ppm tocopherol, 1500 ppm tocotrienol and 1300 ppm sterols dissolved in neutral oil.

100 g of the raffinate phase was mixed thoroughly with 100 g of 4-formylmorpholine by stirring. Following interruption of the mixing process, separation into two liquid, co-existing phases was allowed to take place, and samples were taken from either phase for analysis. The oil-rich raffinate phase minus the extractant contained 320 ppm carotene and 0.01 wt. % free fatty acids. Tocopherols and sterols were present in traces only. The extract phase contained 1500 ppm carotene, 0.07 wt. % free fatty acids, 30 ppm tocopherols, 90 ppm tocotrienols and 30 ppm sterols dissolved in neutral oil.

EXAMPLE 6

100 g of palm oil containing 420 ppm carotene, 4.0 wt. % free fatty acids and approx. 96 wt. % glycerides was mixed with 100 g of 4-formylmorpholine at 50° C. by stirring. Following interruption of the mixing process, complete separation of the two liquid phases was allowed to take place, and samples were taken from both co-existing phases, the compositions of which were analysed. The oil-rich raffinate phase minus the extractant contained approx. 97 wt. % glycerides, 3.0 wt. % free fatty acids and 390 ppm carotene. The extract phase rich in 4-formylmorpholine, minus the extractant, contained 1600 ppm carotene, approx. 68 wt. % glycerides, and approx. 32 wt. % free fatty acids. Without the free fatty acids content, the neutral oil content was 2350 ppm.

EXAMPLE 7

100 g of deacidified palm oil containing 280 ppm carotene and 0.28 wt. % free fatty acids was mixed at 60° C. with 100 g of dimethylformamide by stirring. Following interruption of the mixing process, the two liquid phases were allowed to separate, and samples were then taken from the two co-existing phases. Analysis showed for the two liquid phases minus the extractant the following composition: a) raffinate phase: 200 ppm carotene, approx. 99.8 wt. % glycerides, 0.2 wt. % free fatty acids; b) extract phase: 950 ppm carotene, approx. 90.5 wt. % glycerides and 9.5 wt. % free fatty acids.

EXAMPLE 8

200 g of palm oil containing 95.52 wt. % of neutral oil, 4.34 wt. % free fatty acids, 0.02 wt. % α-tocopherol, 0.02 wt. % α-tocotrienol, 0.04 wt. % γ-tocotrienol, 0.01 wt. % δ-tocotrienol, 0.01 wt. % stigmasterol, 0.03 wt. % sitosterol and 430 ppm carotene was mixed at 90° C. with 200 g of 4-formylmorpholine and 10 g of heptane. Following interruption of the mixing process and separation of the two liquid phases formed, samples were taken from either phase and analysed. Loading of the extractant amounted to 2.7 wt. %. The raffinate phase minus extractant contained 96.98 wt. % of neutral oil, 2.90 wt. % free fatty acids, 0.02 wt. % α-tocopherol, 0.02 wt. % α-tocotrienol, 0.03 wt. % γ-tocotrienol, 0.01 wt. % δ-tocotrienol, 0.01 wt. % stigmasterol, 0.02 wt. % sitosterol and 380 ppm carotene. The extract phase was comprised of 72.75 wt. % neutral oil, 26.60 wt. % free fatty acids, 0.07 wt. % α-tocopherol, 0.08 wt. % α-toco-trienol, 0.26 wt. % δ-tocotrienol, 0.08 wt. % δ-tocotrienol, 0.05 wt. % stigmasterol, 0.11 wt. % sitosterol and 940 ppm carotene.

What is claimed is:

1. A process for extracting carotenes from carotene-containing materials, comprising:

extracting a carotene-containing material with an extractant comprising at least one member selected from the group consisting of acetonitrile, N-methylpyrrolidone, N,N-dimethylformamide, N,N-dimethylacetamide, 4-formylmorpholine, 4-acetylmorpholine, 4-methylmorpholine, and 4-phenylmorpholine, with the formation of two liquid phases, one of which is a carotene-depleted raffinate phase and the other one is a carotene-enriched extract phase; and separating the two liquid phases.

2. The process of claim 1, wherein said carotene-containing material is selected among fats and oils of biological origin consisting of: palm oil, soybean oil, rapeseed oil, corn oil, hemp oil, sunflower oil, olive oil, linseed oil, beet oil, castor oil, sesame oil, cocoa butter, rice germ oil, cottonseed oil, grape kernel oil, wheat germ oil, palm kernel oil, coconut oil, peanut oil, safflower oil, and mixtures thereof.

3. The process of claim 1, wherein said extraction is performed in countercurrent flow.

4. The process of claim 1, wherein the extractant is removed from at least one of said raffinate phase and extract phase by liquid-liquid extraction with water.

5. The process of claim 1, wherein the extractant is removed from at least one of said raffinate phase and extract phase by stripping with nitrogen, steam or with vapor of an alcohol, selected from the group consisting of methanol, ethanol, isopropanol, and mixtures thereof.

6. The process of claim 1, wherein the extractant is removed from at least one of said raffinate phase and extract phase by extraction with dense gases, selected from the group consisting of carbon dioxide, propane, propene, butane, and mixtures thereof.

7. The process of claim 1, wherein the carotenes are recovered from said extract phase by crystallization and filtration.

8. The process of claim 1, wherein the carotene-containing material, prior to extracting, has been subjected to a pretreatment selected from degumming, filtration, deacidification, or combinations thereof.

9. The process of claim 1, wherein the extraction is performed at a temperature in the range of from about 20 to about 120° C.

10. The process of claim 5 wherein the extractant is removed from at least one of said raffinate phase and extract phase by stripping under reduced pressure.

11. The process of claim 6 wherein the extractant is removed from at least one of said raffinate phase and extract phase by extraction under near-critical conditions.

12. The process of claim 9 wherein the range is from about 40 to about 80° C.

13. A process for extracting carotenes from carotene-containing materials, comprising: extracting a carotene-containing material with an extractant comprising at least one member selected from the group consisting of a mixture of N-methylpyrrolidone and methanol, a mixture of 4-methylmorpholine and water, and a mixture of 4-formylmorpholine and methanol, with the formation of two liquid phases, one of which is a carotene-depleted raffinate phase and the other one is a carotene-enriched extract phase; and separating the two liquid phases.

14. The process of claim 13 wherein the mixture of N-methylpyrrolidone and methanol contains 30 to 70 wt. % methanol.

15. The process of claim 14 wherein the mixture contains 40 to 60 wt. % methanol.

16. The process of claim wherein the mixture of 4-methylmorpholine and water contains 3 to 20 wt. % water.

17. The process of claim 16 wherein the mixture contains 5 to 15 wt. % water.

18. The process of claim 13 wherein the mixture of 4-formylmorpholine and methanol contains to 30 wt. % methanol.

19. The process of claim 18 wherein the mixture contains 5 to 10 wt. % methanol.

20. The process of claim 13, wherein the extraction is performed at a temperature in the range of from about 20 to about 120° C.

21. The process of claim 20 wherein the range is from about 40 to about 80° C.

* * * * *